(12) United States Patent
Locke et al.

(10) Patent No.: US 12,102,748 B2
(45) Date of Patent: Oct. 1, 2024

(54) GEL-BLOCKING CONNECTION ASSEMBLY FOR ABSORBENT NEGATIVE PRESSURE DRESSING

(71) Applicant: Solventum Intellectual Properties Company, Maplewood, MN (US)

(72) Inventors: Christopher Brian Locke, Bournemouth (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 17/634,210

(22) PCT Filed: Aug. 11, 2020

(86) PCT No.: PCT/IB2020/057545
§ 371 (c)(1),
(2) Date: Feb. 9, 2022

(87) PCT Pub. No.: WO2021/033077
PCT Pub. Date: Feb. 25, 2021

(65) Prior Publication Data
US 2022/0323666 A1      Oct. 13, 2022

Related U.S. Application Data

(60) Provisional application No. 62/889,454, filed on Aug. 20, 2019.

(51) Int. Cl.
*A61M 1/00*         (2006.01)
*A61F 13/05*        (2024.01)
*A61F 13/15*        (2006.01)

(52) U.S. Cl.
CPC .............. *A61M 1/912* (2021.05); *A61F 13/05* (2024.01); *A61M 1/915* (2021.05); *A61F 2013/15073* (2013.01)

(58) Field of Classification Search
None
See application file for complete search history.

(56) References Cited

U.S. PATENT DOCUMENTS 1,355,846 A   10/1920   Rannells
2,547,758 A    4/1951   Keeling
(Continued)

FOREIGN PATENT DOCUMENTS

AU        550575 B2    3/1986
AU        745271 B2    3/2002
(Continued)

OTHER PUBLICATIONS

International Search Report and Written Opinion for Corresponding Application No. PCT/IB2020/057545 mailed Dec. 10, 2020.
(Continued)

*Primary Examiner* — Philip R Wiest
*Assistant Examiner* — Matthew Wrubleski

(57) ABSTRACT

A dressing includes a manifold layer and a drape coupled to the manifold layer and configured to seal the manifold layer over a wound. The drape has an opening extending therethrough. A connection pad is positioned at the opening and configured to couple the dressing to a tube. The connection pad includes an outer ring coupled to the drape and a center dimple extending away from the drape and defining a volume between the center dimple and a plane defined by the outer ring. The dressing also includes an absorbent manifolding structure positioned between the center dimple and the manifold layer and formed to substantially match a shape of the volume.

15 Claims, 7 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,782,787 A * | 7/1998 | Webster | A61F 13/023 602/56 |
| 6,071,267 A | 6/2000 | Zamierowski | |
| 6,077,526 A * | 6/2000 | Scully | A61F 13/00042 424/443 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0167631 A1 * | 7/2008 | Greer | A61M 1/915 602/53 |
| 2010/0069863 A1 * | 3/2010 | Olson | A61M 1/915 604/385.01 |
| 2010/0324516 A1 * | 12/2010 | Braga | A61M 1/916 604/378 |
| 2012/0302979 A1 * | 11/2012 | Locke | A61M 1/915 604/319 |
| 2014/0121615 A1 | 5/2014 | Locke et al. | |
| 2014/0163491 A1 | 6/2014 | Schuessler et al. | |
| 2014/0309574 A1 * | 10/2014 | Cotton | A61F 13/2005 602/44 |
| 2015/0080788 A1 | 3/2015 | Blott et al. | |
| 2015/0100045 A1 * | 4/2015 | Allen | A61M 1/96 604/543 |
| 2015/0119830 A1 | 4/2015 | Luckemeyer et al. | |
| 2018/0353339 A1 * | 12/2018 | Locke | A61F 13/0223 |
| 2019/0151159 A1 * | 5/2019 | Gowans | A61F 13/0203 |

FOREIGN PATENT DOCUMENTS

| | | |
|---|---|---|
| AU | 755496 B2 | 12/2002 |
| CA | 2005436 A1 | 6/1990 |
| CN | 107669405 A * | 2/2018 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| | | | |
|---|---|---|---|
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2011135287 A1 | 11/2011 | |
| WO | WO-2015173547 A1 * | 11/2015 | ....... A61F 13/00008 |
| WO | 2017196888 A1 | 11/2017 | |
| WO | 2018229012 A1 | 12/2018 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 pages English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All—Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. @ Therapy Clinical Guidelines: A Reference Source for Clinicians; Jul. 2007.

\* cited by examiner

GEL-BLOCKING CONNECTION ASSEMBLY FOR ABSORBENT NEGATIVE PRESSURE DRESSING

CROSS-REFERENCE TO RELATED APPLICATIONS

This application claims the benefit of priority to U.S. Provisional Application No. 62/889,454, filed on Aug. 20, 2019, which is incorporated herein by reference in its entirety.

BACKGROUND

The present disclosure relates generally to the field of wound therapy, and more particularly to dressings for use in negative pressure wound therapy.

Negative pressure wound therapy (NPWT) is a type of wound therapy that involves applying negative pressure (relative to atmospheric pressure) to a wound bed to promote wound healing. Typically, a dressing is sealed over a wound bed and air is pumped out of the dressing to create a negative pressure at the wound bed. In some NPWT systems, wound exudate and other fluid is pumped out of the dressing and collected by a therapy system.

In other NPWT systems, air is pumped out of the dressing while the dressing is used to absorb fluid from the wound. In some such systems, it is preferable for air to be drawn to the pump while fluid or other wound exudate is prevented from reaching the pump, such that the pump is protected from contamination or other damage that may be caused by such fluid or other exudate contacting the pump. Accordingly, assemblies for protecting the pump from contact with fluid or other wound exudate while also allowing the pump to remove air from the dressing are desirable.

SUMMARY

One implementation of the present disclosure is a dressing. The dressing includes a manifold layer and a drape coupled to the manifold layer and configured to seal the manifold layer over a wound. The drape has an opening extending therethrough. A connection pad is positioned at the opening and configured to couple the dressing to a tube. The connection pad includes an outer ring coupled to the drape and a center dimple extending away from the drape and defining a volume between the center dimple and a plane defined by the outer ring. The dressing also includes an absorbent manifolding structure positioned between the center dimple and the manifold layer and formed to substantially match a shape of the volume.

In some embodiments, the absorbent manifolding structure includes a hydrophobic porous member combined with an air permeable superabsorbent material configured to gel-block upon exposure to fluids.

In some embodiments, the absorbent manifolding structure is configured to allow a flow of air therethrough when the absorbent manifolding structure is in contact with less than a threshold amount of fluid.

In some embodiments, absorbent manifolding structure includes a polymer manifolding material and a superabsorbent material. The superabsorbent material may be configured to swell in response to contact with fluid. The absorbent manifolding structure may include a sintered polyethylene mixed with the superabsorbent material. The absorbent manifolding structure may restrict the flow of air therethrough when the superabsorbent material is swollen. For example, the absorbent manifolding structure may prevent the flow of air through a first region of the absorbent manifolding structure and allow the flow of air through a second region of the absorbent manifolding structure when the superabsorbent material is swollen at the first region and superabsorbent material is non-swollen at the second region.

In some embodiments, the absorbent manifolding structure includes a fluid-activated dye configured to provide a change in color of the absorbent manifolding structure when fluid fills the absorbent manifolding structure.

In some embodiments, the dressing includes a dye in the tube configured to provide an indication representative of fluid in the tube.

Another implementation of the present disclosure is a dressing. The dressing includes a manifold layer, a drape coupled to the manifold layer and configured to seal the manifold layer over a wound, a connection pad positioned at a hole extending through the drape and configured to couple the dressing to a tube, a felted foam layer positioned between the connection pad and the manifold layer, and a fluid-activated blocking layer coupled to the felted foam layer. The fluid-activated blocking layer is configured to allow a flow of air therethrough from the manifold layer to the tube when in contact with less than a threshold amount of fluid and to restrict the flow of fluid therethrough when in contact with more than the threshold amount of fluid.

In some embodiments, the fluid-activated blocking layer includes a gel-blocking sintered polymer.

In some embodiments, wherein the fluid-activated blocking layer comprises a superabsorbent material. For example, the fluid-activated blocking layer may include a perforated superabsorbent laminate. The perforated superabsorbent laminate may include a plurality of perforations extending therethrough. Each perforation is configured to close when a portion of the superabsorbent material proximate the perforation absorbs fluid.

In some embodiments, the fluid-activated blocking layer includes a first microporous film. The dressing may also include a second microporous film.

Another implementation of the present disclosure is a wound therapy system. The wound therapy system includes a dressing sealable over a wound, and a tube coupled to the dressing and configured to connect the dressing and a pump. The tube includes a hydrophobic outer ring extending for a length of the tube, a fluid-activated inner ring positioned within the hydrophobic outer ring and extending for at least a portion of the length of the tube, and a channel extending through the fluid activated inner ring and the hydrophobic outer ring. The channel is configured to allow a flow of air through the tube from the dressing to the pump. The fluid-activated inner ring is configured to reduce a diameter of the channel when the fluid-activated inner ring is exposed to fluid.

In some embodiments, the fluid-activated inner ring is configured to close the channel when the fluid-activated inner ring is exposed to fluid such that the fluid-activated ring prevents the flow of fluid from the dressing to the pump.

In some embodiments, the fluid-activated inner ring is configured to swell into the channel when exposed to fluid.

In some embodiments, the hydrophobic outer ring comprises perforations extending therethrough from an exterior surface of the tube to the fluid-activated inner ring. The fluid-activated inner ring is configured to soften when exposed to fluid and, when the fluid-activated inner ring is softened, to collapse into the channel when a pressure differential is established between the channel and ambient pressure.

In some embodiments, a dye is included in the tube. The dye is configured to indicate a presence of fluid in the tube.

DETAILED DESCRIPTION

Figure 1:
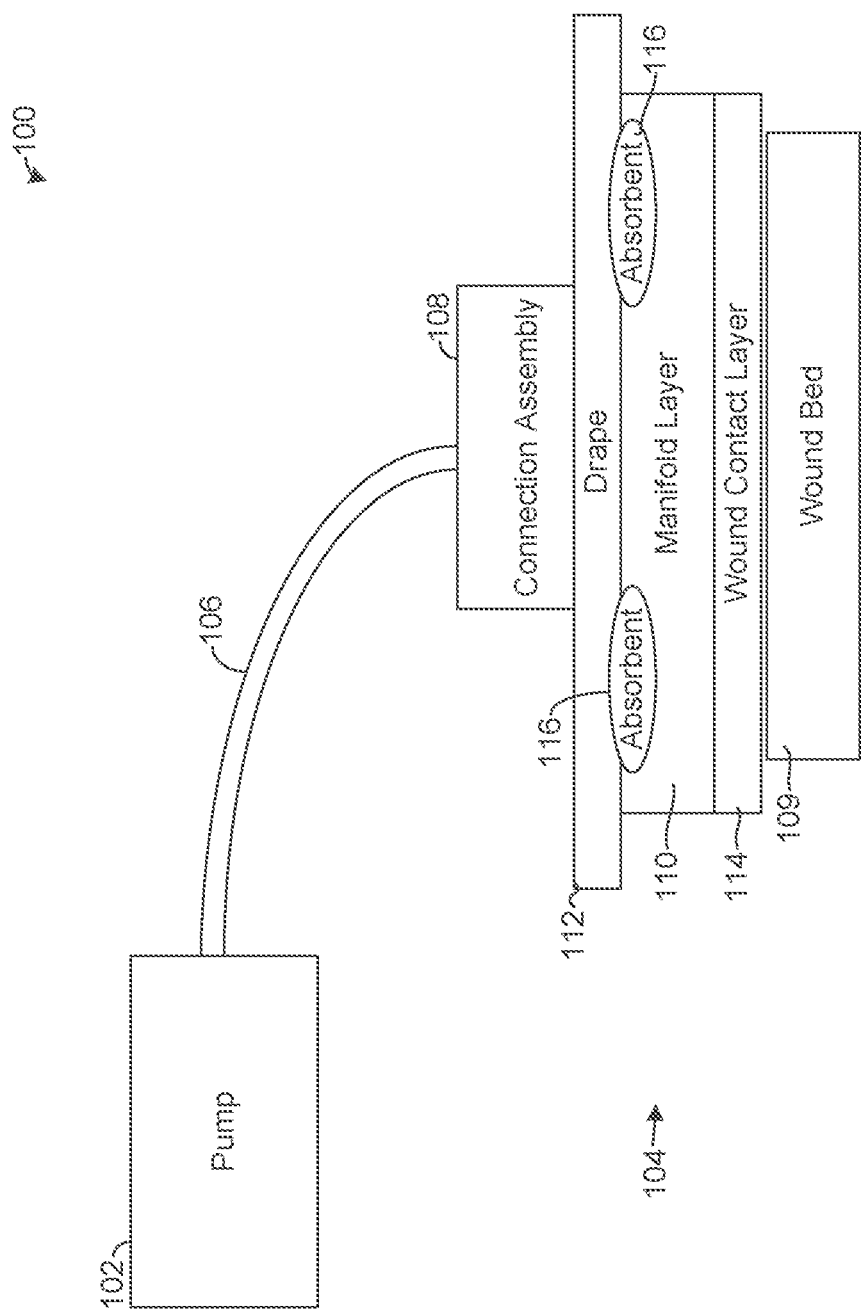
FIG. 1 is a block diagram of a negative pressure wound therapy (NPWT) system with an absorbent dressing, according to an exemplary embodiment.

Referring now to FIG. 1, a negative pressure wound therapy (NPWT) system 100 is shown, according to an exemplary embodiment. The NPWT system 100 includes a pump 102 pneumatically communicable with a dressing 104 via tube 106. The tube 106 is coupled to the dressing 104 by a connection assembly 108. The dressing 104 is shown as sealed over a wound bed 109. The wound bed 109 is a tissue wound of a patient, for example a laceration, burn, sore, trauma wound, chronic wound, etc.

The dressing 104 allows a negative pressure to be maintained at the wound bed 109 while absorbing fluid from the wound bed 109. The dressing 104 thereby provides both negative pressure and a high level of fluid absorption. The dressing 104 is shown to include drape 112, a manifold layer 110, a wound contact layer 114, and absorbent deposits 116. It should be understood that the dressing 104 is one example of an absorbent negative pressure dressing and that many embodiments are possible, for example as shown and described in U.S. Provisional Patent Application 62/732,285, filed Sep. 17, 2018, incorporated by reference herein in its entirety.

The drape 112 is configured to seal the wound contact layer 114, the manifold layer 110, and the absorbent deposits 116 over the wound bed 109. For example, the drape 112 may include an adhesive ring coupleable to the patient's skin surrounding the wound bed 109. The drape 112 may include a material that substantially prevents leaking of air therethrough to facilitate creation and maintenance of a negative pressure at the manifold layer 110 (i.e., in a volume between the drape 112 and the wound bed 109). The drape 112 may also include a material with a high moisture vapor transfer rate to facilitate evaporation of fluid from the absorbent deposits 116 to the ambient air through the drape 112.

The wound contact layer 114 provides an interface between the dressing 104 and a wound. In some embodiments, the wound contact layer 114 is configured to prevent ingrowth of the wound bed 109 to the dressing and to facilitate removal of the dressing 104 while minimizing damage to the healing tissue of the wound bed 109. The wound contact layer 114 includes a film, for example a silicone film. The wound contact layer 114 may be perforated or otherwise formed to allow for the flow of air and fluid therethrough.

The manifold layer 110 is configured to allow airflow therethrough to facilitate the distribution of negative pressure across the wound bed 109. In some embodiments, the manifold layer 110 may include an open-celled foam, for example a foam material marketed as GRANUFOAM™ by ACELITY™. The manifold layer 110 is also configured to allow fluid to flow therethrough, from the wound bed 109 to the absorbent deposits 116.

The absorbent deposits 116 are configured to absorb fluid, for example wound exudate from the wound bed 109. The absorbent deposits 116 may include a superabsorbent material. Various arrangements and configurations of the absorbent deposits 116 are included in various embodiments. In some embodiments, the absorbent deposits 116 are included as a superabsorbent laminate positioned between the drape 112 and the manifold layer 110, with channels extending therethrough to allow airflow therethrough. It should be understood that various configurations of absorbent dressings 104 are contemplated by the present disclosure and can be compatible with the connection assembly 108, which is described in detail with reference to FIGS. 2-9. The absorbent deposits 116 and the dressing 104 are configured such that the absorbent deposits 116 absorb fluid to approximately a full capacity of the absorbent deposits 116 before fluid passes into or is absorbed by the connection assembly 108 as described below.

The connection assembly 108 is configured to couple the dressing 104 to a tube 106, which is coupled to a pump 102. The connection assembly 108 is positioned at a hole extending through the drape 112 such that the connection assembly 108 is in fluid communication with the manifold layer 110. As shown in FIGS. 2-9 and described in detail with reference thereto, the connection assembly 108 is configured to allow airflow between the manifold layer 110 and the pump 102 while restricting the flow of fluid therebetween. The tube 106 is configured to provide an airway that allows air to flow from the connection assembly 108 to the pump 102. In some embodiments, for example as shown in FIG. 10 and described in detail with reference thereto, the tube 106 is configured to prevent the flow of fluid therethrough.

The pump 102 is operable to pump air out of the dressing 104 via the tube 106 to create and maintain a negative pressure at the wound bed 109. In some embodiments, the pump 102 is electrically powered and the NPWT system 100 includes power systems and control circuitry to power and control operation of the pump 102. For example, the NPWT system 100 may include one or more pressure sensors or various other sensors that collect data used to control the pump 102 to maintain a negative pressure at the wound bed 109. In some embodiments, the pump 102 is manually-powered, such that a user may manipulate the pump 102 to draw air out of the dressing 104 as desired by the user. For example, the pump 102 may be spring-loaded to gradually pull air from the dressing 104 for a duration of time following a compression of the pump 102 by the user.

The NPWT system 100 is thereby configured to provide a negative pressure at the wound bed 109 while also facilitating absorption of fluid from the wound bed 109 by the dressing 104.

Figure 2:
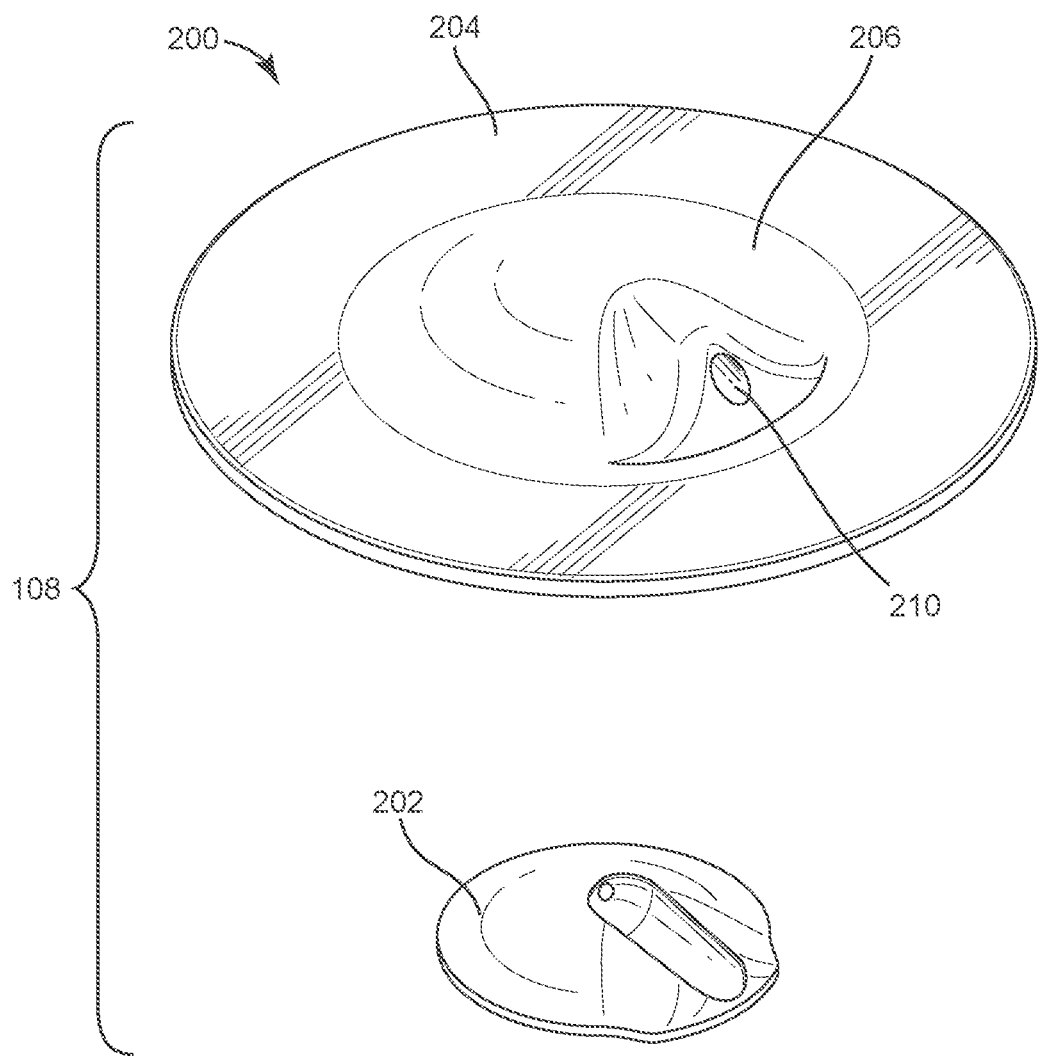
FIG. 2 is perspective, exploded view of a first embodiment of a connection assembly for use with the NPWT system of FIG. 1.
Figure 3:
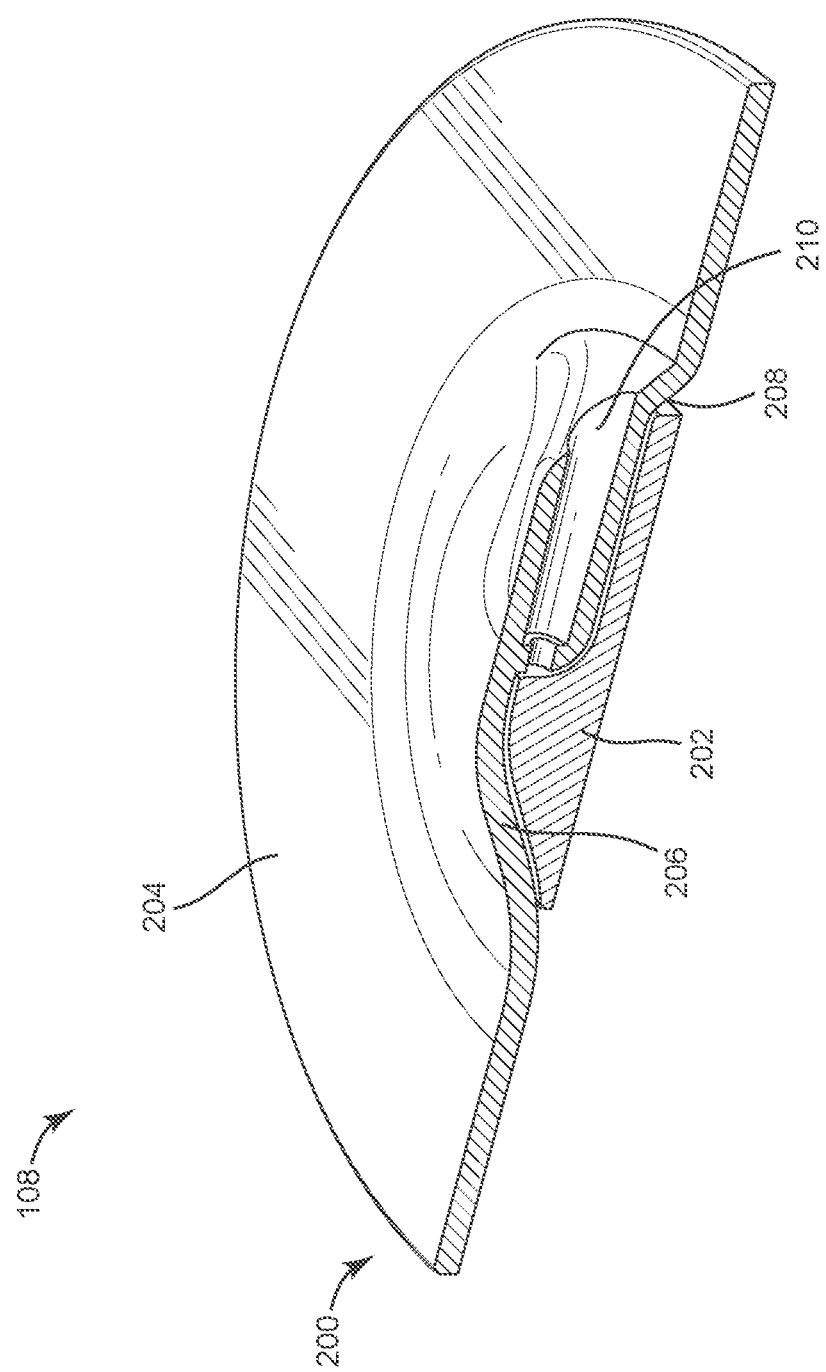
FIG. 3 is a perspective, bisected view of the connection assembly of FIG. 2, according to an exemplary embodiment.
Figure 4:
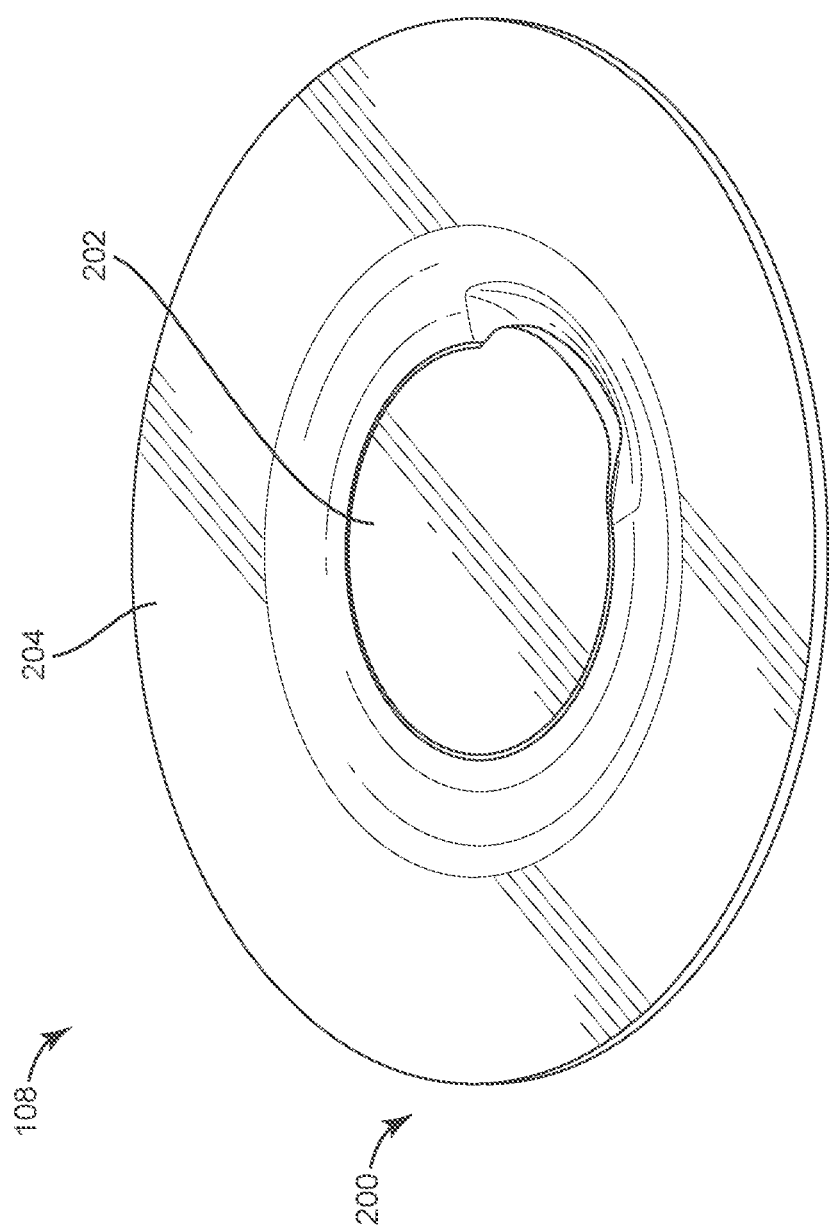
FIG. 4 is a perspective, bottom view of the connection assembly of FIGS. 2-3, according to an exemplary embodiment.

Referring now to FIGS. 2-4, an various views of the connection assembly 108 are shown, according to an exemplary embodiment. As shown in FIGS. 2-4, the connection assembly 108 includes a connection pad 200 and an absorbent manifolding structure 202.

The connection pad 200 is configured to couple the dressing 104 to the tube 106. The connection pad 200 includes an outer ring 204 that surrounds a center dimple 206. The outer ring 204 is configured to be coupled to the drape 112. When the outer ring 204 is coupled to the drape, the center dimple 206 extends away from the drape 112. The center dimple 206 thereby defines an inner volume 208 between the center dimple 206 and a plane defined by the outer ring 204. The connection pad 200 also includes a tube conduit 210 configured to receive the tube 106.

The absorbent manifolding structure (disc, insert, layer, etc.) 202 is formed to have a shape that substantially matches a shape of the inner volume 208. Accordingly, the absorbent manifolding structure 202 is configured to fit substantially within the inner volume 208 and the inner volume 208 is configured to receive the absorbent manifolding structure 202. In the example shown, the absorbent manifolding structure 202 substantially fills the inner volume 208. By fitting within the inner volume 208, the absorbent manifolding structure 202 can be selectively included or not included with the NPWT system 100 without requiring a change in the design or manufacturing process for the dressing 104 or the connection pad 200.

As shown in FIGS. 2-4, the absorbent manifolding structure 202 is positioned in the inner volume 208 and positioned between the tube conduit 210 and the dressing 104 such that airflow from the dressing 104 to the tube 106 must pass through the absorbent manifolding structure 202. The absorbent manifolding structure 202 is configured to allow airflow therethrough (i.e., between the dressing 104 and the tube 106) when the absorbent manifolding structure 202 has not absorbed a threshold amount of fluid, and to prevent airflow therethrough when the absorbent manifolding structure 202 has absorbed more than a threshold amount of fluid.

According to the illustrated embodiments, the absorbent manifolding structure 202 is shown to include a sintered polymer material (e.g., sintered polyethylene) mixed with a superabsorbent material. The sintered polymer material is formed with pores (channels, spaces, airways, etc.) such that air and fluid can pass through the sintered polymer material. Each pore may have a size within a range between approximately 20 microns and 60 microns. The superabsorbent material is dispersed in the sintered polymer material and is configured to absorb fluid and swell when in contact with fluid. In the absorbent manifolding structure 202, when the superabsorbent material swells to absorb fluid (e.g., more than a threshold amount of fluid), the swollen superabsorbent material closes (gel-blocks, fills, blocks, obstructs, etc.) the pores of the sintered polymer material and restricts the flow of air and fluid through the absorbent manifolding structure 202. The absorbent manifolding structure 202 is thereby configured to allow airflow therethrough when substantially dry, while substantially preventing the flow of air and fluid therethrough when more than a threshold amount of fluid is absorbed by the sintered polymer material. In some embodiments, the air flow through the absorbent manifolding structure 202 is between approximately 160 ml/min and 480 ml/min at an air pressure of 300 Pa. The absorbent manifolding structure 202 thereby facilitates the pump 102 in drawing a negative pressure at the dressing 104 while substantially preventing fluid from the wound bed 109 from reaching the pump 102 (damaging the pump 102, contaminating the pump 102, etc.).

The blocking effect provided by the superabsorbent material may be localized within the absorbent manifolding structure 202 to areas (regions, spots, etc.) of the absorbent manifolding structure 202 in contact with fluid. For example, a first region of the absorbent manifolding structure 202 may include swollen superabsorbent (having absorbed fluid) that blocks the flow of air and fluid through the first region, while a second region of the absorbent manifolding structure 202 is substantially dry (i.e., not in contact with a significant amount of fluid) and therefore allows air to flow through the second region. This regional independence may allow airflow through the absorbent manifolding structure 202 to remain open for an increased amount of time.

In some embodiments, the absorbent manifolding structure 202 includes a fluid-activated dye. In such embodiments, the dye is released and/or changes color in response to contact with fluid. The connection pad 200 may be translucent or transparent such that the dye is visible through the connection pad 200. The absorbent manifolding structure 202 may thereby be configured to provide a visual indication that the absorbent manifolding structure 202 has absorbed fluid to a user (patient, caregiver, etc.). In other embodiments, the tube 106 includes a fluid-activated dye configured to release and/or change color in response to contact with fluid, such that a change in color in the tube indicates that fluid has passed through the absorbent manifolding structure 202. The inclusion of a dye may thereby facilitate a user in determining when to remove the dressing 104 and/or make other changes to wound therapy.

Figure 5:
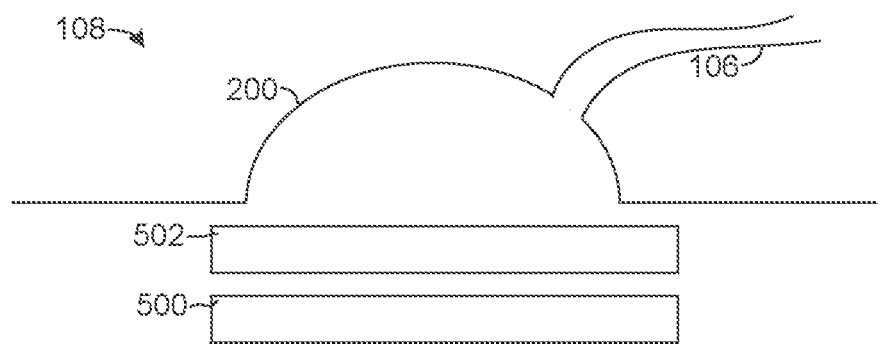
FIG. 5 is a cross-sectional view of a second embodiment of a connection assembly for use with the NPWT system of FIG. 1.

Referring now to FIG. 5, a second embodiment of the connection assembly 108 is shown, according to an exemplary embodiment. As shown in FIG. 5, the connection assembly 108 includes the connection pad 200, a felted foam layer 500, and a gel-blocking sintered polymer layer 502 positioned between the connection pad 200 and the felted foam layer 500. As shown in FIG. 5, the felted foam layer 500 and the gel-blocking sintered polymer layer 502 are positioned under the connection pad 200 (i.e., between the center dimple 206 and the dressing 104. In other embodiments, the felted foam layer 500 and the gel-blocking sintered polymer layer 502 are formed to fit within the center dimple 206 similar to the examples of FIGS. 2-4.

The felted foam layer 500 is configured to allow airflow therethrough and to resist the flow of fluid therethrough such that fluid in the dressing 104 is directed to the absorbent deposits 116 or other wicking or absorbent structure of the dressing 104 when absorbent capacity is available in the dressing 104. The felted foam layer 500 thereby substantially minimizes or restricts the flow of fluid into the connection assembly 108 when absorbent capacity is available in the dressing 104. When the dressing is full (i.e., when the absorbent capacity of the dressing 104 is met), the felted foam layer 500 is configured to allow fluid to pass therethrough from the manifold layer 110 to the gel-blocking sintered polymer layer 502. Accordingly, passage of fluid through the felted foam layer 500 is associated with a full dressing 104. The felted foam layer 500 may include three to five times felted foam, where the foam is a same or similar foam as the manifold layer 110 (i.e., processed to be permanently compressed to a fraction of the original thickness of the foam material of the manifold layer 110).

The gel-blocking sintered polymer layer 502 is configured to allow air to flow therethrough when the gel-blocking sintered polymer layer 502 has absorbed less than a threshold amount of fluid, and to prevent air and fluid from flowing therethrough when the gel-blocking sintered polymer layer 502 has absorbed more than a threshold amount of fluid. The gel-blocking sintered polymer layer 502 includes a sintered polymer material (e.g., sintered polyethylene) mixed with a superabsorbent material. The sintered polymer material is formed with pores (channels, spaces, airways, etc.) such that air and fluid can pass through the sintered polymer material. Each pore may have a size within a range between approximately 20 microns and 60 microns. The superabsorbent material is dispersed in the sintered polymer material and is configured to absorb fluid and swell when in contact with fluid. When the superabsorbent material of the gel-blocking sintered polymer layer 502 swells to absorb fluid (e.g., more than a threshold amount of fluid), the swollen superabsorbent material closes (gel-blocks, fills, blocks, obstructs, etc.) the pores of the sintered polymer material and restricts the flow of air and fluid through the absorbent manifolding structure 202. The absorbent manifolding structure 202 is thereby configured to allow airflow therethrough when substantially dry, while substantially preventing the flow of air and fluid therethrough when more than a threshold amount of fluid is absorbed by the sintered polymer material. The gel-blocking sintered polymer layer 502 may also include a fluid-activated dye configured to provide a visual indication of fluid reaching the gel-blocking sintered polymer layer 502.

The gel-blocking effect provided by the superabsorbent material may be localized within the gel-blocking sintered polymer layer 502 to regions (areas, spots, etc.) of the gel-blocking sintered polymer layer 502 in contact with fluid. For example, a first region of the gel-blocking sintered polymer layer 502 may include swollen superabsorbent (having absorbed fluid) that blocks the flow of air and fluid through the first region, while a second region of the gel-blocking sintered polymer layer 502 is substantially dry (i.e., not in contact with a significant amount of fluid) and therefore allows air to flow through the second region. This regional independence may allow airflow through the gel-blocking sintered polymer layer 502 to remain possible for an increased amount of time.

Figure 6:
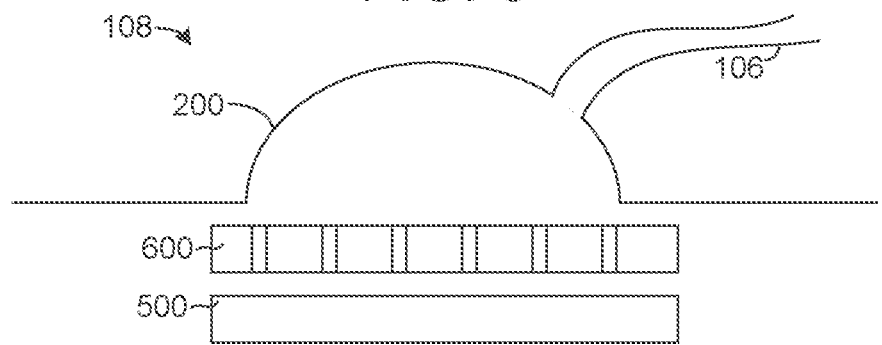
FIG. 6 is a cross-sectional view of a third embodiment of a connection assembly for use with the NPWT system of FIG. 1.

Referring now to FIG. 6, a third embodiment of the connection assembly 108 is shown. As shown in FIG. 6, the connection assembly 108 includes the connection assembly, the felted foam layer 500 and a perforated superabsorbent laminate 600 positioned between the felted foam layer 500 and the perforated superabsorbent laminate 600. As shown in FIG. 6, the felted foam layer 500 and the perforated superabsorbent laminate 600 are positioned under the connection pad 200 (i.e., between the center dimple 206 and the dressing 104. In other embodiments, the felted foam layer 500 and/or the perforated superabsorbent laminate 600 are formed to fit within the center dimple 206 similar to the examples of FIGS. 2-4.

The perforated superabsorbent laminate 600 is configured to allow air to flow therethrough when the perforated superabsorbent laminate 600 has absorbed less than a threshold amount of fluid, and to prevent air and fluid from flowing therethrough when the perforated superabsorbent laminate 600 has absorbed more than a threshold amount of fluid. The perforated superabsorbent laminate 600 includes one or more membranes (e.g., films, hydrophilic membranes, etc.) and a superabsorbent material. For example, in one embodiment, the perforated superabsorbent laminate 600 includes a hydrophilic membrane layer, a superabsorbent material positioned on the hydrophilic membrane layer, and a film layer coupled to the hydrophilic foam layer and configured to confine the superabsorbent material between the film layer and the hydrophilic membrane layer. Various embodiments of super-absorbent laminates are described in U.S. Patent Application No. 62/788,036, filed Jan. 3, 2019, the entire disclosure of which is incorporated by reference herein.

In the example of FIG. 6, the perforated superabsorbent laminate 600 includes multiple perforations (holes, channels, airways, pores, etc.) extending therethrough (e.g., approximately 5 perforations, approximately 10 perforations, approximately 100 perforations, etc.). The perforations may have a diameter between approximately 1 mm and 2 mm and may be spaced to maintain structural integrity of the perforated superabsorbent laminate 600. For example, the perforations may be distributed within a radial spacing of approximately 4-5 mm over the perforated superabsorbent laminate 600. The perforations allow air to flow through the perforated superabsorbent laminate 600 via the perforations.

When the superabsorbent material of the perforated superabsorbent laminate 600 absorbs fluid, the superabsorbent material swells, including into the perforations to narrow or close (block, fill, shut) the perforations. When the superabsorbent material is swollen to close all perforations, the perforated superabsorbent laminate 600 substantially prevents the flow of air and fluid through the perforated superabsorbent laminate 600. Additionally, swelling of the superabsorbent material may be localized to regions where fluid is in contact with the superabsorbent laminate 600 (i.e., where fluid has passed through the felted foam layer 500). Accordingly, in one example, a first region of the superabsorbent laminate 600 is exposed to fluid and the superabsorbent material at the first region is swollen to block one or more perforations of the first region, while a second region of the superabsorbent laminate is not exposed to fluid and the superabsorbent material at the second region is not swollen such that perforations at the second region remain open. In this example, airflow is blocked at the first region where airflow is allowed via the perforations of the second region. Accordingly, the perforations may be characterized as an array of fluidly-activated micro-valves.

Figure 7:
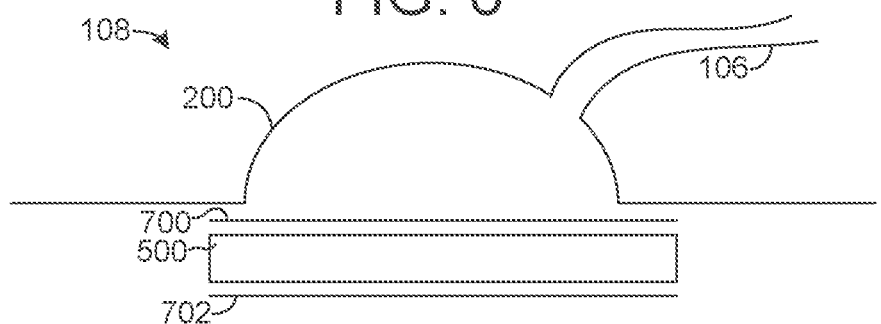
FIG. 7 is a cross-sectional view of a fourth embodiment of a connection assembly for use with the NPWT system of FIG. 1.

Referring now to FIG. 7, a fourth embodiment of the connection assembly 108 is shown, according to an exemplary embodiment. As shown in FIG. 7, the connection assembly 108 includes the connection pad 200, the felted foam layer 500, a first microporous film layer 702 coupled to the felted foam layer 500, and a second microporous film layer 700 positioned between the felted foam layer 600 and the connection pad 200. The felted foam layer 500 is positioned between the first microporous film layer 702 and the second microporous film layer 700. The first microporous film layer 702 and the second microporous film layer 700 are configured to allow air to flow therethrough. The first microporous film layer 702 and the second microporous film layer 700 are also configured to resist a flow of fluid therethrough (i.e., allows a low rate of fluid to pass therethrough). The combination of the first microporous film layer 702, the felted foam layer 500, and the second microporous film layer 700, arranged in series between the manifold layer 110 and the connection pad 200, thereby restricts (limits, reduces, substantially prevents) fluid from passing through all three layers 500, 700, 702 to reach the tube 106. The first microporous film layer 702, the felted foam layer 500, and the second microporous film layer 700 may be positioned below the connection pad 200 as shown in FIG. 7 or may be positioned in the inner volume 208 of the connection pad 200 similar to the embodiments of FIGS. 2-4.

Figure 8:
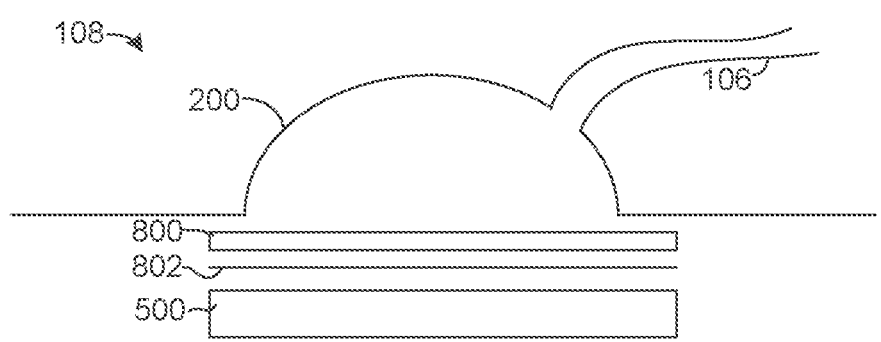
FIG. 8 is a cross-sectional view of a fifth embodiment of a connection assembly for use with the NPWT system of FIG. 1.

Referring now to FIG. 8, a fifth embodiment of the connection assembly 108 is shown, according to an exemplary embodiment. As shown in FIG. 8, the connection assembly 108 includes the connection pad 200, the felted foam layer 500, a superabsorbent fiber layer 800 positioned between the felted foam layer 500 and the connection pad 200 and a fusible fiber layer 802 positioned between the felted foam layer 500 and the connection pad 200. The fusible fiber layer 802 is configured to couple the superabsorbent fiber layer 800 to the felted foam layer 500. In some embodiments and with some manufacturing processes, the fusible fiber layer 802 may be omitted and the superabsorbent fiber layer 800 may adhere directly to the felted foam layer 500. The felted foam layer 500, the superabsorbent fiber layer 800, and the fusible fiber layer 802 may be positioned below the connection pad 200 as shown in FIG. 8 and/or may be positioned in the inner volume 208 of the connection pad 200 similar to the example of FIGS. 2-4.

The superabsorbent fiber layer 800 is open to airflow when dry, i.e., such that air can flow therethrough from the felted foam layer 500 to the connection pad 200. The superabsorbent fiber layer 800 is configured to absorb fluid and swell to retain the fluid. When fluid is absorbed by the superabsorbent fiber layer 800, the swelling of the superabsorbent fiber layer 800 closes airways through the superabsorbent fiber layer 800, thereby substantially preventing airflow through the superabsorbent fiber layer 800. Various regions of the superabsorbent fiber layer 800 may swell and block airflow independent, for example such that fluid has been absorbed and airflow is blocked at a first region of the superabsorbent fiber layer 800 while fluid has not been absorbed and air can flow through a second region of the superabsorbent fiber layer 800. In some embodiments, the superabsorbent fiber layer 800 may include a superabsorbent fiber sold as Oasis Type 2577 Super Absorbent Fibre by Technical Absorbents Limited or a superabsorbent fiber sold as M631/113 by Freudenberg.

Various other embodiments having a similar arrangement as that shown in FIGS. 5-8 are also possible. For example, in some embodiments a superabsorbent material (e.g., in a granular form) is deposited on the felted foam layer 500. The superabsorbent material may be suspended in an organic dry solvent such as a ketone or alcohol and may be coated on the felted foam layer 500, and may behave in a similar manner as the superabsorbent fiber layer 800 of FIG. 8. The superabsorbent material may be arranged as a cross-linked hydrogel printed (deposited, etc.) on the felted foam layer 500 in a pattern that allows airflow therethrough while having sufficient coverage to block the flow of fluid therethrough when swollen. As another example, a perforated hydrogel sheet or a hydrogel coated mesh may be included to allow air to flow through the sheet or mesh when dry and substantially prevent the flow of air and fluid through the sheet or mesh when in contact with at least a threshold amount of fluid.

Figure 9:
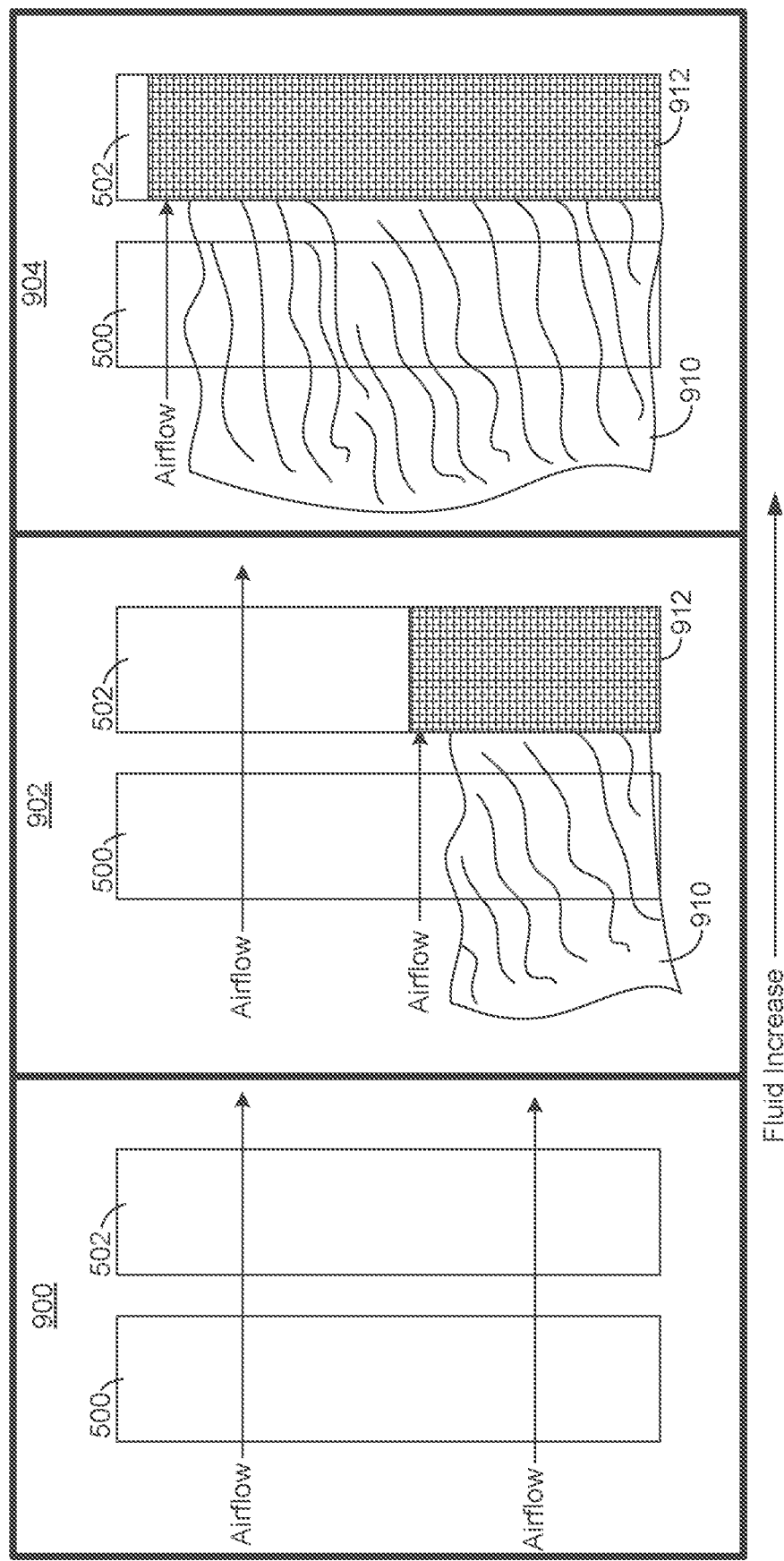
FIG. 9 is a series of illustrations depicting the behavior of the second embodiment of the connection assembly when in contact with fluid, according to an exemplary embodiment.
Figure 10:
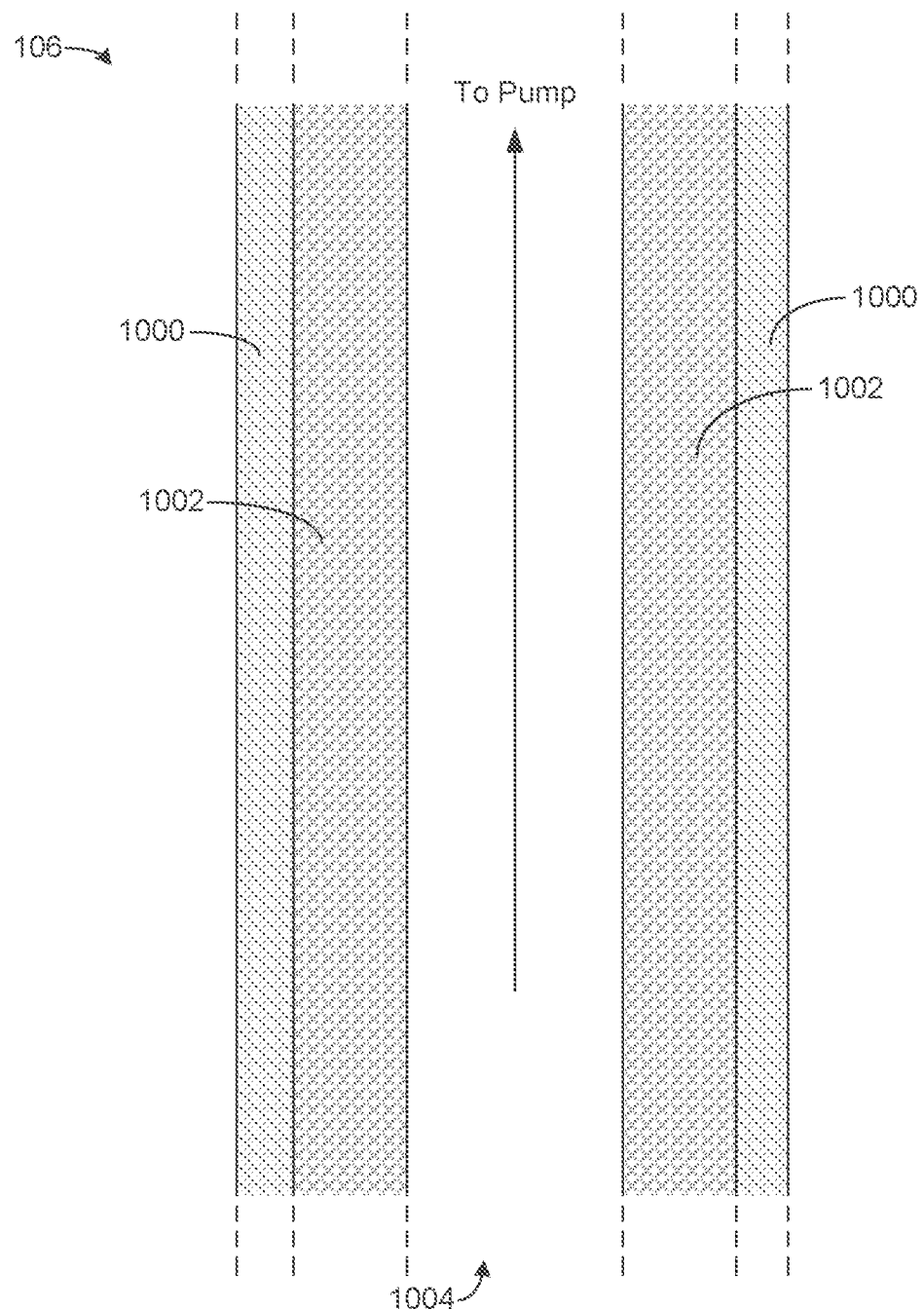
FIG. 10 is a cross-sectional view of a tube for use with the NPWT system of FIG. 1, according to an exemplary embodiment.

Referring now to FIG. 9, an illustration depicting the behavior of the second embodiment of the connection assembly 108 (i.e., as in FIG. 5) when in contact with fluid, according to an exemplary embodiment. FIG. 9 shows three frames, arranged in chronological order to show change over time. In the first frame 900, the felted foam layer 500 and the gel-blocking sintered polymer layer 502 are not exposed to fluid. Accordingly, airflow is permitted through all regions (portions, areas, etc.) of the felted foam layer 500 and the gel-blocking sintered polymer layer 502. In the first frame 900, the pump 102 can draw air out of the manifold layer 110 via the tube 106 and connection assembly 108 at a maximum airflow rate to establish a negative pressure at the wound bed 109.

Between the first frame 900 and the second frame 902, the felted foam layer 500 is exposed to fluid 910. For example, a maximum absorption capacity of the dressing 104 (e.g., of the absorbent deposits 116) may have been met such that the excess fluid is directed into the felted foam layer 500. The fluid 910 has passed through the felted foam layer 500 to the gel-blocking sintered polymer layer 502. In response to contact with the fluid 910, the superabsorbent material of the gel-blocking sintered polymer layer 502 has swollen in a gel-blocked region 912 of the sintered polymer layer 502. The gel-blocked region 912 substantially prevents the flow of air and fluid through the gel-blocked region 912 of the gel-blocking sintered polymer layer 502. As shown in the second frame 902, the gel-blocked region 912 is only a portion of the gel-blocking sintered polymer layer 502. Accordingly, airflow is still permitted through other areas of the gel-blocking sintered polymer layer 502 as indicated in the second frame 902. The rate of airflow through the connection assembly 108 to the pump 102 may be lower in the second frame 902 relative to the first frame 900.

Between the second frame 902 and the third frame 904, the amount of fluid 910 at the felted foam layer 500 and the gel-blocking sintered polymer layer 502 continues to increase. In the third frame 904, substantially the entirety of the gel-blocking sintered polymer layer 502 is exposed to fluid. The superabsorbent material has swollen across substantially the entirety of the gel-blocking sintered polymer layer 502. Accordingly, the gel-blocked region 912 has expanded relative to the second frame 902 to block airflow through substantially the entirety of the gel-blocking sintered polymer layer 502. The flow of air and fluid through the gel-blocking sintered polymer layer 502 (and therefore the connection assembly 108) is thereby substantially prevented.

Referring now to FIG. 10, a cross-sectional view of an embodiment of the tube 106 is shown, according to an exemplary embodiment. The tube 106 may be used with various embodiments of the NPWT system 100 including with various embodiments of the connection assembly 108. The tube 106 is configured to be coupled to the tube conduit 210 of the connection pad 200 and the pump 102.

As shown in FIG. 10, the tube 106 includes a hydrophobic outer ring 1000 and a fluid-activated inner ring 1002. A central channel 1004 extends approximately along a central axis of the fluid-activated inner ring 1002. The tube 106 is configured to allow airflow therethrough (i.e., through the central channel 1004) when the fluid-activated inner ring 1002 is substantially dry and to block the flow of fluid and air therethrough when the fluid-activated inner ring 1002 is exposed to a threshold amount of fluid.

In the example of FIG. 10, the hydrophobic outer ring 1000 includes a plasticized PVC or polyurethane tube (e.g., a suitable material for standard medical-grade tubing). The hydrophobic outer ring 1000 surrounds and is coupled to the fluid-activated inner ring 1002. The fluid-activated inner ring 1002 is positioned within the hydrophobic outer ring 1000. The hydrophobic outer ring 1000 and fluid-activated inner ring 1002 may make up a full length of the tube 106 or may be included as one or more segments of the tube 106 (e.g., added as an accessory to an existing tubeset).

In some embodiments, the hydrophobic outer ring 1000 is configured to swell in response to contact with fluid. For example, the hydrophobic outer ring 1000 may include a superabsorbent material configured to absorb fluid and swell to retain the fluid. In such embodiments, the hydrophobic outer ring 1000 may be configured to resist expansion, i.e., such that the fluid-activated inner ring 1002 primarily expands into the central channel 1004 when exposed to fluid. Accordingly, as fluid enters the tube 106, the cross-sectional area of the central channel 1004 is reduced partially or completely by the fluid-activated inner ring 1002, thereby reducing the rate of air or fluid flow through the central channel 1004 and/or preventing the flow of air or fluid through the central channel 1004.

In other embodiments, the fluid-activated inner ring 1002, when substantially dry, is configured to provides structural support that prevents the fluid-activated inner ring 1002 (and, in some embodiments, the hydrophobic outer ring 1000) from collapsing inward due to a pressure differential between the ambient air and the interior of the central channel 1004 (as established by the pump 102). In such embodiments, the fluid-activated inner ring 1002 is configured to soften when in contact with fluid, thereby reducing the rigidity of the fluid-activated inner ring 1002 and the ability of the fluid-activated inner ring 1002 to provide structural support for the tube 106. In some such embodiments, the hydrophobic outer ring 1000 includes perforations that allow communication of ambient air pressure to the fluid-activated inner ring 1002, which may cause the fluid-activated inner ring 1002 to collapse under a pressure differential between the ambient air and the interior of the central channel 1004 (i.e., without requiring collapse of the hydrophobic outer ring 1000). In other embodiments, the hydrophobic outer ring 1000 may collapse under the pressure differential when the structural support of the fluid-activated inner ring 1002 is reduced.

Accordingly, when the fluid-activated inner ring 1002 is exposed to a threshold amount of fluid, the pressure differential between the ambient air and the central channel 1004 causes the fluid-activated inner ring 1002 (and, in some embodiments, the hydrophobic outer ring 1000) and to collapse inwards, reducing or eliminating a cross-sectional area of the central channel 1004. The flow of air and fluid is thereby restricted or prevented by the tube 106 in response to fluid entering the tube 106.

In either embodiment, the closing of the central channel 1004 may be made reversible. For example, the fluid-activated inner ring 1002 may return to its original form as fluid returns to the dressing 104 from the tube 106 (e.g., drawn into the superabsorbent deposits 116 as fluid from the superabsorbent deposits 116 evaporates to the ambient environment).

In some embodiments, the tube 106 includes a fluid-activated dye configured to be released and/or to change color in response to exposure to fluid. In such embodiments, the tube 106 is transparent or translucent such that the dye is visible in the tube. The dye may thereby facilitate a user in determining when a dressing should be removed and/or planning other modifications to wound therapy for the wound bed 109.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

Other arrangements and combinations of the elements described herein and shown in the Figures are also contemplated by the present disclosure. The construction and arrangement of the systems and apparatuses as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

What is claimed is:

1. A dressing, comprising:
    a manifold layer;
    a drape coupled to the manifold layer and configured to seal the manifold layer over a wound, the drape having an opening extending therethrough;
    a connection pad positioned at the opening and configured to couple the dressing to a tube, the connection pad comprising:
        an outer ring coupled to the drape; and
        a center dimple extending away from the drape and defining a volume between the center dimple and a plane defined by the outer ring; and
    an absorbent manifolding structure positioned between the center dimple and the manifold layer and formed to substantially match a shape of the volume.

2. The dressing of claim 1, wherein the absorbent manifolding structure comprises a hydrophobic porous member combined with an air permeable superabsorbent material configured to gel-block upon exposure to fluids.

3. The dressing of claim 1, wherein the absorbent manifolding structure fills the volume between the center dimple and the plane defined by the outer ring and is configured to allow a flow of air therethrough when the absorbent manifolding structure is in contact with less than a threshold amount of fluid.

4. The dressing of claim 1, wherein the absorbent manifolding structure comprises a polymer manifolding material and a superabsorbent material.

5. The dressing of claim 4, wherein the superabsorbent material is configured to swell in response to contact with fluid.

6. The dressing of claim 5, wherein the absorbent manifolding structure restricts the flow of air therethrough when the superabsorbent material is swollen.

7. The dressing of claim 6, wherein the absorbent manifolding structure prevents the flow of air through a first region of the absorbent manifolding structure and allows the flow of air through a second region of the absorbent manifolding structure when the superabsorbent material is swollen at the first region and superabsorbent material is non-swollen at the second region.

8. The dressing of claim 4, wherein the absorbent manifolding structure comprises a sintered polyethylene mixed with the superabsorbent material.

9. The dressing of claim 1, wherein the absorbent manifolding structure comprises a fluid-activated dye configured to provide a change in color of the absorbent manifolding structure when fluid fills the absorbent manifolding structure.

10. The dressing of claim 1, comprising a dye in the tube configured to provide an indication representative of fluid in the tube.

11. A dressing, comprising: a manifold layer; a drape coupled to the manifold layer and configured to seal the manifold layer over a wound; a connection pad positioned at a hole extending through the drape and configured to couple the dressing to a tube; a felted foam layer positioned to substantially fill an inner volume of the connection pad; and a fluid-activated blocking layer coupled to the felted foam layer, the fluid-activated blocking layer configured to allow a flow of air therethrough from the manifold layer to the tube when in contact with less than a threshold amount of fluid and to restrict the flow of fluid therethrough when in contact with more than the threshold amount of fluid.

12. The dressing of claim 11, wherein the fluid-activated blocking layer comprises a gel-blocking sintered polymer.

13. The dressing of claim 11, wherein the fluid-activated blocking layer comprises a superabsorbent material coupled to the felted foam layer by a fusible fiber layer.

14. The dressing of claim 11, wherein the fluid-activated blocking layer comprises a perforated superabsorbent laminate with a plurality of perforations extending therethrough, each perforation configured to close when a portion of the superabsorbent material proximate the perforation absorbs fluid.

15. The dressing of claim 11, wherein the fluid-activated blocking layer comprises a first microporous film and a second microporous film, the felted foam layer positioned between the first microporous film and the second microporous film.

* * * * *